United States Patent [19]
Reisser et al.

[11] Patent Number: 5,931,996
[45] Date of Patent: Aug. 3, 1999

[54] COLORED ALUMINUM PIGMENTS, PROCESS FOR PRODUCING THEM AND THEIR USE

[75] Inventors: Wolfgang Reisser, Gossau, Switzerland; Denise Mebarek, Büchenbach, Germany

[73] Assignee: Eckart-Werke Standard, Bronzepulver, Germany

[21] Appl. No.: 08/875,008

[22] PCT Filed: Jan. 16, 1996

[86] PCT No.: PCT/DE96/00085

§ 371 Date: Sep. 2, 1997

§ 102(e) Date: Sep. 2, 1997

[87] PCT Pub. No.: WO96/22336

PCT Pub. Date: Jul. 25, 1996

[30] Foreign Application Priority Data

Jan. 18, 1995 [DE] Germany .................. 195 01 307

[51] Int. Cl.$^6$ ....................................... C09C 1/64
[52] U.S. Cl. ............... 106/404; 106/31.65; 106/493; 106/499; 106/504; 428/403; 428/469; 428/472; 523/200; 524/441
[58] Field of Search .................. 106/404, 493, 106/499, 504, 31.65; 428/403, 469, 472; 523/200; 524/441

[56] References Cited

U.S. PATENT DOCUMENTS

| | | | |
|---|---|---|---|
| 4,076,551 | 2/1978 | Bernhard et al. | 106/291 |
| 4,158,074 | 6/1979 | Uchiyama et al. | 106/404 |
| 4,328,042 | 5/1982 | Ostertag et al. | 106/308 B |
| 4,867,793 | 9/1989 | Franz et al. | 106/415 |
| 4,885,032 | 12/1989 | Okai et al. | 106/404 |
| 4,978,394 | 12/1990 | Ostertag et al. | 106/404 |
| 5,037,475 | 8/1991 | Chida et al. | 106/403 |
| 5,127,951 | 7/1992 | Imasato et al. | 106/404 |
| 5,261,955 | 11/1993 | Nadkarni | 106/404 |
| 5,372,638 | 12/1994 | Depue et al. | 106/404 |
| 5,374,306 | 12/1994 | Schlegel et al. | 106/404 |
| 5,401,306 | 3/1995 | Schmid et al. | 106/417 |
| 5,662,738 | 9/1997 | Schmid et al. | 106/404 |
| 5,718,753 | 2/1998 | Suzuki et al. | 106/404 |

FOREIGN PATENT DOCUMENTS

| | | |
|---|---|---|
| 0 328 906 A2 | 8/1989 | European Pat. Off. . |
| 41 40 295 | 9/1993 | Germany . |
| 61-130375 | 6/1986 | Japan . |
| 01110568 | 4/1989 | Japan . |
| 91/04293 | 4/1991 | WIPO . |

*Primary Examiner*—Anthony Green
*Attorney, Agent, or Firm*—James A. Lucas

[57] ABSTRACT

The invention concerns colored aluminum pigments comprising flake-form aluminum substrates which are coated with a metal oxide layer. The pigments are produced by a process which involves the steps of mixing a ground color pigment with a flake-form aluminum in the presence of a solvent. A metal acid ester is then added to the mixture and is then hydrolyzed to form a metal oxide layer on the aluminum substrate, followed by removal of the solvent and drying of the pigment. The pigments are useful as special-effect pigments in paints, lacquers, coatings, plastic materials, printing inks and cosmetic preparation.

28 Claims, No Drawings

COLORED ALUMINUM PIGMENTS, PROCESS FOR PRODUCING THEM AND THEIR USE

BACKGROUND OF THE INVENTION

The invention concerns coloured aluminium pigments, a process for the production thereof and use thereof.

Aluminium pigments are used widely in coatings as special-effect pigments. The term special-effect pigments is used to denote pigments which have a directed reflection at oriented, metallic or highly light-refractive particles of a predominantly flat configuration (German Standard DIN 55944). They are always of plate-like or flake-like configuration and have very large particle diameters compared with dye pigments. Their optical properties are determined by reflection and interference. Depending on transparency, absorption, thickness, singlelayer or multi-layer structure, the special-effect pigments exhibit a metallic shine, a pearl shine, interference or interference reflection. The main area of use are in the cosmetics and automobile sector, and in addition in colouring plastic materials, paints, leather coatings, in the printing industry and in the ceramic industry. (For a comprehensive representation of the technical background, see W. Ostertag, Nachr. Chem. Techn. Lab. 1994, 9, 849.).

The special-effect pigments which are most frequently used are aluminium flakes and coated mica flakes, wherein aluminium pigments exhibit a typical metal shine and coated mica flakes exhibit a typical pearl shine.

In recent years the need for coloured special-effect pigments has increased greatly. Therefore for example oxide-covered copper and brass flakes, substrates which are coated with transition metal oxides, such as muscovite, phlogopite or glass, guanine single-crystals (fish silver), BiOCl-single crystals, flake-form haematite single-crystals, flake-form phthalocyanines or crushed thin multi-layer films with a Fabry-Perot-structure are used as special-effect pigments.

In order to achieve colour effects inter alia aluminium pigments are also mixed with transparent dye pigments. The colouristic options with that method are however limited insofar as it is not possible in that way to achieve interference effects and therefore the pigments do not have a pearl shine. However, because of the transparency, interference pigments with a pearl shine, which are mostly based on coated mica flakes, have a poorer covering capability than aluminium pigments. Attempts have therefore been made to produce pigments with the good covering capability of aluminium flakes and the colouristic options of interference pigments, by colouring aluminium pigments.

U.S. Pat. No. 4,328,042 and EP-A-0 033 457 describe the production of gold-coloured aluminium pigments by the deposition of iron oxide, wherein iron pentacarbonyl is oxidised with oxygen in a fluidised bed of the aluminium flakes, the bed being produced by fluidisation with inert gas. The disadvantage of that procedure is the very high level of technological expenditure.

U.S. Pat. No. 5,037,475 describes the production of aluminium pigments which are coloured by fixing colour pigments on the metal surface. The colour pigments are fixed by way of carboxyl group-bearing polymers. A protective layer can be applied by polymerisation, to improve the adhesion. However the pigments produced in that way have only a low level of colour intensity.

WO 91/04293 (PCT/US90/05236) describes the colouring of aluminium pigments by fixing poly-coated colour pigments from aqueous solvents on the metal surfaces by way of electrostatic forces. In that situation the coating result depends in a complex manner on the type of aluminium pigment, the nature of the polymer coating on the colour pigments, the solvent composition and the pH-value.

EP-A-0 328 906 discloses titanium dioxide-coated metal pigments, inter alia also aluminium pigments, which are produced by hydrolysis of an organic titanate ester compound, for example tetraisopropoxytitanium, in the presence of the metal flakes which are suspended in an organic medium, at pH of from 4 to 8. Various colour shadescan be achieved with that process by varying the thickness of the titanium dioxide layer. Maintaining specific conditions is crucial for producing the coated pigments. The pH-value must be in the range of from 4 to 8 and the dropping speed used in adding the titanate ester must be in the range of from $1.0 \times 10^{-7}$ to $1.0 \times 10^{-4}$ mole per minute and $m^2$ metal surface area. Therefore that process cannot be used on a large technical scale. In addition the coated pigments must be calcined after the drying operation in order to achieve colour effects as a suitable layer structure is achieved only by removal of the water from the metal oxide layer. Because of the low melting point of aluminium however the calcination operation can only be carried out with a very great deal of difficulty when involving coated aluminium pigments.

U.S. Pat. No. 4,978,394 describes the production of titanium dioxide-coated aluminium pigments by chemical vapour deposition (CVD), wherein titanium tetrachloride is reacted at a low level of concentration with water vapour in a fluidised bed in the presence of hot aluminium particles. This process also suffers from the disadvantage of expensive technology.

U.S. Pat. No. 4,158,074 discloses the production of coloured aluminium pigments by coating with a film comprising hydrated aluminium oxide and hydrated metal oxide. The film is produced by the treatment of fine aluminium flakes or plates in an alkaline solution of an iron, nickel, cobalt, zinc or copper salt at elevated temperature at a pH-value of from 8 to 12, that is to say by an electrochemical reaction of the metal salts. In that way it is possible to produce gold-coloured pigments, and by the addition of chelating agents, also black-brown and grey-white pigments.

U.S. Pat. No. 5,261,955 describes a sol-gel-process for the production of coloured metal pigments, wherein the metal flakes or plates are dispersed in a sol of an inorganic salt, for example an aqueous alkaline zirconium oxide sol, the flakes or plates coated with the sol are dispersed after filtration in a solution of an inorganic compound, for example cobalt nitrate, in an organic solvent, and a sol-gel layer is formed on the flakes by heating. The large number of individual steps involved in that process means that a high level of apparatus expenditure is also required.

JP-A-61-130375 discloses a gold-coloured aluminium pigment, produced by the treatment of aluminium powder pigment with dichromate, sodium fluoride and surface-active agents in acid solution, drying and subsequent treatment with a fatty acid derivative. Colour shades other than gold cannot be achieved using this method.

German laid-open application (DE-OS) No 41 40 295 describes pigments comprising carrier materials in flake or plate form, preferably mica, which are coated with an inorganic matrix containing metal oxides and/or dye particles in the sub-micrometre range. The operation of coating the substrates is effected out of acid aqueous suspensions by the hydrolysis of metal salts, preferably titanium tetrachloride, in the presence of metal oxide and/or dye particles. However it is not possible to colour aluminium flakes using that process because under those conditions the aluminium particles quickly break down.

U.S. Pat. No. 3,067,052 discloses coloured aluminium particles which are produced by the oxidation of aluminium powder with KMnO$_4$-solution, possibly with the addition of a reducing agent. The colour shade of those pigments is golden, possibly also with a greenish or reddish shade, depending on the respective reducing agent used.

DE 25 57 796 discloses a coloured aluminium pigment which is coated with a metal oxide layer containing carbon black as the colour pigment. The proportion of colour pigment is 10% by weight at a maximum. According to that specification, larger amounts of colour pigment have a detrimental effect on shine and colour.

DE 36 17 430 discloses coated coloured pigments, the base pigment comprising mica. Coatings containing colour pigment are not named in that document. The colour effects of the described pigments are produced by interference.

DE 42 23 383 describes metal sulphide-coated substrates, wherein the metal sulphide layer does not contain any colour pigments.

DE 42 23 384 (U.S. Pat. No. 5,374,306) discloses metal oxide-coated aluminium substrates without a colour pigment component. According to that publication, the lowest possible content of carbon, that is to say lubricants and organic impurities, is decisive in regard to achieving good shine effects. The substrates must therefore be pre-treated by heating in an oxygen-bearing atmosphere.

JP-1-110 568 (Patent Abstracts of Japan, Section C, Volume 13 (1989) No 331 (C-622)) discloses aluminium substrates coated with thin oxide layers, without a colour pigment component, the colour effects thereof being produced by interference.

For the stated reasons, the processes for the production of coloured pigments on a mica basis cannot be used to produce aluminium pigments, in respect of which however there is a high level of interest because of the higher covering capability and the metal shine. The known processes for colouring aluminium pigments however afford only few colour shades, predominantly in the gold range, and for the major part are very expensive in terms of apparatus. Therefore there was still a need for aluminium pigments which are coloured in different colour shades, and a need for a process which is simple in terms of apparatus, for the production of those coloured aluminium pigments.

SUMMARY OF THE INVENTION

The object of the present invention is to provide such pigments and a process for the production thereof.

That object is attained by the provision of aluminium pigments comprising aluminium substrates in flake or lamellar form, which are coated with a coloured pigment-bearing metal oxide layer. The pigments according to the invention are produced from flake-form aluminium substrates by the metal oxide layer being produced not by precipitation of the metal salts from an aqueous solution, but by the controlled hydrolysis of metal acid esters in the presence of colour pigments in an organic solvent by means of a sol-gel process which is carried out in one step. The aluminium pigments according to the invention present a very wide range of different colour shades, thus for example blue, red, violet and gold, and a metallic shine.

In the pigment according to the invention the amount of colour pigment is from 15 to 40% by weight, preferably at least 20% by weight and the amount of metal oxide is preferably from 3 to 95% by weight, in each case with respect to the aluminium substrate.

An embodiment of the invention concerns coloured aluminium pigments which are obtainable by a procedure whereby:

a) one or more types of colour pigments is ground in the usual manner, b) the ground material is mixed with aluminium pigments and one or more organic solvents, c) one or more metal acid esters is added, d) 1 to 5 times the amount of water which is stoichiometrically necessary for complete hydrolysis of the metal acid esters is added, e) after the end of the reaction the volatile constituents are removed from the mixture in the usual manner, and f) the pigments obtained are dried.

In a preferred embodiment the aluminium pigments are not subjected to a degreasing treatment before step b) is performed.

In a further/preferred embodiment a part of the metal acid ester is already added to the colour pigment or pigments in step a) during the grinding operation, and the amount of metal acid ester is correspondingly reduced in step c).

In a further embodiment step a) involves the addition of a usual additive which improves pigment dispersion.

Besides the pigments themselves the invention also concerns a process for the production thereof, including above-mentioned steps a) to f).

In a further embodiment of the process according to the invention the reaction mixture obtained in step d) is heated to a temperature of between 40° C. and the boiling point of the solvent added in step b) and/or a basic catalyst is added.

The drying operation in step f) is preferably effected at less than 200° C., still more preferably at less than 150° C., and most desirably at less than 100° C., in a vacuum, for example at 90° C. in a vacuum drying cabinet.

DETAILED DESCRIPTION OF THE INVENTION

The colour pigments that can be used are conventional organic and inorganic colour pigments. Preferably those colour pigments which have a high level of transparency and colour-fastness are used. The man skilled in the art can direct himself to the literature (for example G. Buxbaum, Industrial Inorganic Pigments, VCH-Verlag, Weinheim, 1993 and W. Herbst, K. Hunger, Industrielle Organische Pigmente, VCH-Verlag, Weinheim, 1987) and to manufacturer recommendations. Preferred colour pigments are for example C.I. Pigment Blue 15:3, C.I. Pigment Red 179, C.I. Pigment Red 101 and C.I. Pigment Red 202. It is possible to use a single type of pigment or a mixture of a plurality of types of pigments, depending on the respective desired colour shade of the aluminium pigment according to the invention. The color pigments are not in the form of a layer of carbon, metal and/or metal oxide.

The operation of grinding the colour pigments is effected in the usual manner, for example in a bead mill or in a grinding-body mill, for example with zirconium oxide balls. The grinding operation can be effected in a part of the metal acid ester or in a conventional solvent, for example white spirit. Simultaneous use/of white spirit or other solvent and metal acid ester in the grinding operation is also possible. It is also possible to add an additive for improving pigment dispersibility such as for example Antiterra U 80, from Byk-Chemie.

Suitable aluminium pigments in step c) are all conventional aluminium pigments which can be used for decorative coatings. Round aluminium flakes or plates (so-called silver dollars) are preferably used. Particularly preferred is Stapa Metallux of the 2000 type series (from Eckart). Because of their low scatter component those silver dollars permit particularly brilliant colouring effects.

The solvents involved in step b) are organic solvents, preferably water-miscible solvents. Particularly preferred are alcohols such as methanol, ethanol, n-propanol, i-propanol, n-butanol, i-butanol and t-butanol, most preferably i-propanol.

It is also possible, according to the respective needs, after step d) of the process, prior to the end of the reaction, to again add an additional amount of the solvent used in step b). The total amount of the solvent added is preferably from 150 to 300 ml, with respect to 100 g of aluminium substrate.

Suitable metal acid esters are selected from the group comprising alkyl and aryl alcoholates, carboxylates, alkyl alcoholates or carboxylates, substituted with carboxyl residues or alkyl residues or aryl residues, of titanium, zirconium, silicon, aluminium and boron. Particularly preferred are alkyl and aryl alcoholates, in particular $C_1$–$C_6$ alkyl alcoholates such as methanolates, ethanolates, n-propanolates, i-propanolates, n-butanolates, i-butanolates and t-butanolates of the stated metals. These compounds have the general formula $M(OR)_y$, wherein M is titanium, zirconium, vanadium, silicon, aluminium or boron, R is a $C_1$–$C_6$ alkyl, phenyl, xylyl, tolyl or cresyl group, and y is 3 or 4. This type of compound can also be considered as an ester of the metal acids, for example ortho-silicic acid, boric acid, aluminium hydroxide, titanic acid or zirconic acid. Preferably aluminiumtriisopropylate (triisopropylaluminate), titanium tetraisopropylate (tetraisopropyltitanate), polymeric n-butyltitanate, titanium tetraisobutylate (tetraisobutyltitanate), zirconium tetraisopropylate (tetraisopropylzirconate), o-silicic acid tetraethyl ester (tetraethylorthosilicate) and triethylborate (boric acid triethylester) are used. Mixed alcoholates are also possible, that is to say not all residues OR are the same.

In addition it is preferably possible to use acetyl acetonates, acetoacytylacetonates, possibly also substituted by alkyl or alkenyl residues, or acetoacetates of the stated metals. Mixed alcoholates/acetylacetonates, alcoholates/acetoacetylacetonates or alcoholates/acetoacetates, that is to say those metal acid esters which contain both alcoholate residues and also acetylacetonate residues, acetoacetylacetonates or acetoacetate residues are also suitable. Preferred examples of that type of metal acid esters are zirconium, aluminium or titanium acetylacetonate ($Zr(acac)_4$, $Ti(acac)_4$ or $Al(acac)_3$) and diisobutyloleylacetoacetylaluminate or diisopropyloleylacetoacetylacetonate. In addition it is also possible to use mixtures of metal acid esters of different metals which can also be partially condensed, for exaple Dynasil$^R$ (fran Huls), a mixed Al—Si-metal acid ester.

An amount of 15 to 40 g of colour pigment, preferably from 20 to 40 g, and from 0.1 to 0.8 mole of metal acid ester, preferably 0.5 mole, are used relative to 100 g of aluminium substrate with a surface area of about 4 m²/g (BET). When using more than 0.8 mole of metal acid ester, that gives a coloured aluminium pigment with a poor shine and the pigments have a tendency to undesired agglomeration. When using less than 0.1 mole of metal acid ester, the stability of the coated pigment in relation to water and acids is not adequate and it is not possible to achieve adequate adhesion of the colour pigments on the aluminium pigments. If less colour pigment than 15 g is used, the result achieved is an inadequate colour effect, while if more than 40 g of colour pigment is used, the metal shine of the aluminium pigments is excessively greatly covered over.

The crucial consideration for the process according to the invention is the amount of water used in step d), which is from 1 to 5 times the amount necessary for complete hydrolysis of the metal acid ester. A greater excess of water can result in greying of the aluminium pigments and is therefore to be avoided. Therefore 4 to 20 moles of water, preferably from 4.5 to 10 moles, are used in relation to 1 mole of a tetravalent metal acid ester, for example an ortho-silicate, titanate or zironate. Accordingly, from 3 to 15 moles of water, preferably from 3.1 to 8 moles, are used in relation to 1 mole of a trivalent metal acid ester, for example a borate or aluminate. Preferably water from which all salt has been removed is used.

The reaction is conducted at a temperature from ambient temperature up to the boiling point of the solvent or solvents. The temperature depends on the reactivity of the metal acid esters and is adjusted according to requirements.

Particularly when using silicic acid esters, the addition of basic catalysts is preferred, which can be added in step d). It is possible to use the usual basic catalysts. Suitable bases are for example amines such as triethylamine, ethylene diamine or tributyl amine or substituted amines such as dimethylethanolamine or methoxypropylamine. In addition it is also possible to add aminosilanes which have an auto-catalytic effect, for example 3-aminopropyl-trimethoxysilane, N-aminoethyl-3-aminopropyltrimethoxysilane or 3,4,5-dihydroimidazol-1-yl-propyltriethoxysilane. A further addition of base may possibly be effected once again, after some time.

After termination of the reaction, that is to say generally after from 0.5 to 10 hours, the volatile constituents are removed from the reaction mixture in the usual way, for example by distillation or by being pressed out. The pigments are then dried, for example in a vacuum drying cabinet.

The coloured aluminium pigments can be subjected to further processing like conventional aluminium pigments. For example, for many areas of use, it is advantageous to produce non-dusting pastes by the addition of solvents such as hydrocarbons, ethyl acetate, methoxypropanol or butylglycol.

The production process according to the invention for coloured aluminium pigments provides that the metal acid ester is hydrolysed and then condensed, while finally metal oxides are formed in a sol-gel process, which metal oxides are deposited on the aluminium flakes in the form of a dense closed coating and in that case simultaneously fix the colour pigments on the metal surface. The hydrolysis/condensation procedure takes place in a highly complex manner, the beginning of the reaction chain can be represented by the following equations for alcoholate-metal acid ester:

$$M(OR)_y + H_2O \rightarrow (RO)_{y\text{-}1}\text{—M—OH} + ROH \qquad (1)$$

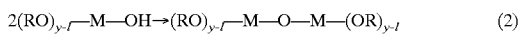

$$2(RO)_{y\text{-}1}\text{—M—OH} \rightarrow (RO)_{y\text{-}1}\text{—M—O—M—}(OR)_{y\text{-}1} \qquad (2)$$

One function of the metal oxide layer lies in providing as an "adhesive" for a strongly adhesive bond between the metal pigment and the colour pigment. A further function of the metal oxide layer is to protect the aluminium pigment from moisture and chemicals. The coloured aluminium pigments according to the invention can therefore be used for example both in conventional solvent-bearing paints and lacquers and also in water-base paints and lacquers.

The novel coloured aluminium pigments according to the invention have particularly great brilliance and a wide spectrum in respect of possible colour shades. The pigments are highly stable. The process is simple to carry out even on a large technical scale and does not require expensive equipment. There is no need for calcination of the pigments as the pigments according to the invention already exhibit excellent brilliance, colour intensity and stability after the drying operation.

The pigments according to the invention can advantageously be used for providing special effects in paints and lacquers, coatings, plastic materials, printing inks and cosmetic preparations.

The invention is described in greater detail hereinafter by means of examples.

EXAMPLE 1

30 g of C.I. Pigment Blue 15:3 is dispersed and ground with 85 g of silicic acid tetraethylester (from Wacker) by means of 300 g zirconium oxide balls (0.7 mm diameter) in a grinding body mill (Red Devil, from the company Union N.J. USA). 100 g of aluminium pigment (Stapa Metallux 2154, BET surface area 3.8 m$^2$/g, from the company Eckart) and 208 ml of isopropanol are added to that dispersion at ambient temperature, and the mixture is stirred for 1 hour. After that a solution of 0.78 g of ethylene diamine and 51.4 g of water from which all salt has been removed is added and the suspension is heated with stirring at 80° C. At intervals each of 1 hour, 0.78 g of ethylene diamine and 51.4 g of isopropanol are also added twice. The mixture is heated for a total of 6 hours. The product is then filtered off and dried at 90° C. in a vacuum cabinet. That gives a metallically shiny, intensively blue aluminium pigment.

Colour pigment: about 19%, S$_i$O$_2$: about 15%; Aluminium pigment: about 65%.

EXAMPLE 2

20 g of C.I. Pigment Red 179 is ground with 56.7 g of silicic acid tetraethylester, 23.3 g of white spirit and 11.4 g of a wetting and dispersing additive (Antiterra U 80, from Byk-Chemie), using the procedure from Example 1. 100 g of aluminium pigment (Stapa Metallux 2154) and 208 ml of isopropanol are added to the mixture. After 0.5 hours of stirring at ambient temperature, 28.3 g of silicic acid tetraethylester is added. After a further 0.5 hour, a solution of 0.78 g of ethylene diamine and 51.4 g of water from which all salt has been removed is added and heated to 80° C. At intervals of 1 hour, 0.78 g of ethylene diamine and 51.4 g of isopropanol are also added twice. After heating for 6 hours the mixture is filtered off and dried at 90° C. in a vacuum cabinet. The result obtained is a metallically shiny, dark-red aluminium pigment.

Colour pigment: about 15%; S$_i$O$_2$: about 17%; Aluminium content: about 69%.

EXAMPLE 3

30 g of C.I. Pigment Blue 15:3 is crushed in 85 g of white spirit in accordance with Example 1. 100 g of aluminium pigment (Stapa Metallux 2154, from Eckart) and 208 ml of isopropanol are added thereto by mixing. After 0.5 hour 85 g of silicic acid tetraethylester is added. After a further 0.5 hour, after the addition of a solution of 0.78 g of ethylene diamine in 51.4 g of water from which all salt has been removed, heating to 80° C. is effected. After 2 hours 0.78 g of ethylene diamine and 51.4 g of isopropanol are added. After heating for 6 hours the mixture is filtered off and dried at 90° C. in the vacuum cabinet. The result obtained is a blue, metallically shiny aluminium pigment.

Colour pigment: about 19%; S$_i$O$_2$: about 15%; Aluminium content: about 65%.

EXAMPLE 4

40 g of C.I. Pigment Red 101 is ground in 90 g of isopropanol, as in Example 1. The further procedure corresponds to that of Example 3. The aluminium pigment used is STAPA Metallux 8154 from Eckart Werke. The result obtained is a metallically shiny, gold aluminium pigment.

Colour pigment: about 24%; S$_i$O$_2$: about 14% Aluminium content: about 61%.

EXAMPLES 5 to 8

In Examples 5 to 8 dispersion of the respective colour pigment is effected as described in Example 3. Colouring is also effected as described in Example 3 with the metal acid esters stated in Table 1 and the amounts of water listed in Table 1.

TABLE 1

|  | Example 5 | Example 6 | Example 7 | Example 8 |
| --- | --- | --- | --- | --- |
| Colour pigment C.I. | Pigment Red 202 | Pigment Red 179 | Pigment Red 202 | Pigment Red 202 |
| Metal acid ester (85 g in each case) Supplier | Zirconium acetyl acetonate ALDRICH | Boric acid triethylester ALDRICH | Diisobutyl-oleylaceto-acetylalu-minate KENRICH | Titanium (IV)isopro-pylate KENRICH |
| Amount of watering | 48 | 32.4 | 34.3 | 26.7 |
| Coloured aluminium pigment Composition: | Metallically shiny red-violet | Metallically shiny red | Metallically shiny red-violet | Metallically shiny red-violet |
| Colour pigment | 19.60% | 16.20% | 18.50% | 18.10% |
| Metal oxide | 11.4% ZrO$_2$ | 21.2% B$_2$O$_3$ | 9.3% Al$_2$O$_3$ | 13.5% TiO$_2$ |
| Aluminium | 69% | 62.30% | 71.20% | 67.40% |

We claim:

1. A colored aluminum pigment comprising a flake-form aluminum substrate coated with a single layer of metal oxide derived from a metal acid ester wherein the layer of the metal oxide contains at least one color pigment, not including carbon, metal and/or metal oxide, said color pigment selected from the group consisting of an organic color pigment, an inorganic color pigment, and a mixture of more than one color pigment present in the oxide layer in an amount of from 15 to 40% by weight with respect to the aluminum substrate.

2. A colored aluminum pigment according to claim 1 wherein the amount of metal oxide in the layer is from 3 to 95% by weight with respect to the aluminum substrate.

3. A colored aluminum pigment according to claim 1 wherein the color pigment is present in the metal oxide layer in an amount of at least 20% by weight with respect to the aluminum substrate.

4. A colored aluminum pigment according to claim 1 wherein said at least one color pigment is an organic color pigment.

5. A product selected from the group consisting of paints, lacquers, coatings, printing inks, plastic materials, and cosmetic preparations containing an amount of the colored aluminum pigment of claim 1 sufficient to impart a metallic shine, to the product.

6. A colored aluminum pigment prepared according to the process comprising the steps of:
   a) grinding at least one color pigment, selected from the group consisting of an organic color pigment, an inorganic color pigment and a mixture of more than one of said color pigments, but not including carbon, metal and/or metal oxide,
   b) forming a mix of the ground color pigment with an aluminum pigment in the presence of a water miscible organic solvent,
   c) adding at least one metal acid ester to the mix,
   d) hydrolyzing the metal acid ester by addition to the mix of from 1 to 5 times the amount of water which is stoichiometrically necessary for complete hydrolysis of the metal acid ester,
   e) at the end of the hydrolysis reaction, removing the organic solvent and other volatile constituents from the reaction mixture, and
   f) drying the resultant aluminum pigment.

7. A colored aluminum pigment according to claim 6 wherein the ground color pigment is mixed with the aluminum pigment and organic solvent without prior degreasing of the aluminum pigment.

8. A colored aluminum pigment according to claim 6 further including the addition of a portion of the total amount of metal acid ester in step a) with the remainder of the acid ester being added in step c).

9. A colored aluminum pigment according to claim 6 further including the addition of a pigment dispersant during the grinding step.

10. A colored aluminum pigment according to claim 6 wherein from 15 to 40 gms. of color pigment and a total of from 0.1 to 0.8 moles of metal acid ester are mixed with 100 gms. of aluminum pigment.

11. A colored aluminum pigment according to claim 6 wherein the metal acid ester comprises at least one ester selected from the group consisting of alkyl alcoholates, aryl alcoholates, carboxylates, alcoholates and carboxylates substituted with carboxyl residues, alkyl residues or aryl residues, of titanium, zirconium, vanadium, silicon, aluminum boron, and mixed condensed metal acid esters of said metals.

12. A colored aluminum pigment according to claim 6 wherein the metal acid ester is selected from the group consisting of triisopropylaluminate, tetraisopropyltitanate, tetraisobutyltitanate, polymeric n-butyltitanate, tetraisopropylzirconate, tetraethylorthosilicate, triethylborate, aluminum acetylacetonate, titanium acetylacetonate, zirconium acetylacetonate, diisobutyloleylacetoacetylaluminate, diisopropyloleylacetoacetylacetonate and mixed Si—Al metal acid esters.

13. A colored aluminum pigment according to claim 6 wherein the mix obtained in step d) is heated to a temperature of from 40 degrees C. to the boiling point of the solvent to remove the solvent and other volatile constituents from the mixture.

14. A colored aluminum pigment according to claim 6 wherein a basic acid catalyst is added to the reaction mixture in step d) followed by removal of the organic solvent and other volatile constituents from the reaction mixture.

15. A colored aluminum pigment according to claim 6 wherein drying is effected in step f) at a temperature of less than 200 degrees C.

16. A colored aluminum pigment according to claim 6 wherein drying is effected in step f) at a temperature of less than about 100 degrees C. in a vacuum.

17. A product selected from the group consisting of paints, lacquers, coatings, printing inks, plastic materials, and cosmetic preparations containing an amount of the colored aluminum pigment of claim 6 sufficient to impart a metallic shine to the product.

18. A process for preparing a colored aluminum pigment comprising the steps of:
   a) grinding at least one color pigment selected from the group consisting of an organic color pigment, an inorganic color pigment, and a mixture of more than one of said color pigments, but not including carbon, metal and/or metal oxides,
   b) forming a mix of the ground color pigment with an aluminum pigment in the presence of a water miscible organic solvent,
   c) adding a metal acid ester to the mix,
   d) hydrolyzing the metal acid ester by addition to the mix of from 1 to 5 times the amount of water which is stoichiometrically necessary for complete hydrolysis of the metal acid ester,
   e) at the end of the hydrolysis reaction, removing the organic solvent and the other volatile constituents from the reaction mixture, and
   f) drying the resultant aluminum pigment.

19. The process according to claim 18 wherein the ground color pigment is mixed with the aluminum pigment and organic solvent without prior degreasing of the aluminum pigment.

20. The process according to claim 18 further including the addition of a portion of metal acid ester in step a) with the remainder of the acid ester being added in step c).

21. The process according to claim 18 further including the addition of a pigment dispersant during the grinding step.

22. The process according to claim 18 wherein from 15 to 40 gms of color pigment and a total of from 0.1 to 0.8 moles of metal acid ester are added relative to 100 gms of aluminum pigment.

23. The process according to claim 18 wherein the metal acid ester comprises at least one ester of a metal selected from the group consisting of alkyl alcoholates, aryl alcoholates, carboxylates, alcoholates and carboxylates substituted with carboxyl residues, alkyl residues of titanium, zirconium, vanadium, silicon, aluminum and boron, and mixed condensed metal acid esters of said metals.

24. The process according to claim 18 wherein the metal acid ester is selected from the group consisting of triisopropylaluminate, tetraisopropyltitanate, tetraisobutyltitanate, polymeric n-butyltitanate, tetraisoproplzirconate, tetraethylorthosilicate, triethylborate, aluminum acetylacetonate, titanium acetylacetonate, zirconium acetylacetonate, diisobutyloleylacetoacetylaluminate, diisopropyloleylacetoacetylacetonate and mixed Si—Al metal acid esters.

25. The process according to claim 18 wherein the metal acid which is hydrolized in step d) is heated to a temperature of from 40 degrees C. to the boiling point of the solvent to remove the solvent and other volatile constituents from the mixture.

26. The process according to claim 18 including the step of adding a basic acid catalyst to the mix during hydrolysis of the metal acid ester.

27. The process according to claim 18 wherein drying is effected in step f) at a temperature of less than 200 degrees C.

28. The process according to claim 18 wherein drying is effected in step c) at a temperature of less than about 100 degrees C. in a vacuum.

* * * * *